United States Patent [19]

Clauss et al.

[11] 4,101,647

[45] Jul. 18, 1978

[54] ORAL DOSAGE FORM FOR X-RAY CONTRAST MEDIA CONTAINING A PHARMACEUTICALLY ACCEPTABLE BASE AND METHOD OF USE THEREOF

[75] Inventors: Wolfram Clauss; Ulrich Speck; Dietmar Jentsch, all of Berlin, Fed. Rep. of Germany

[73] Assignee: Schering Aktiengesellschaft, Berlin and Bergkamen, Fed. Rep. of Germany

[21] Appl. No.: 652,333

[22] Filed: Jan. 26, 1976

[30] Foreign Application Priority Data

Feb. 5, 1975 [DE] Fed. Rep. of Germany ....... 2505218

[51] Int. Cl.$^2$ ............................................. A61K 29/02
[52] U.S. Cl. ............................................. 424/5; 424/4
[58] Field of Search ........................................ 424/4, 5

[56] References Cited

U.S. PATENT DOCUMENTS

| | | | |
|---|---|---|---|
| 2,307,189 | 1/1943 | Bell et al. | 424/5 |
| 2,659,690 | 11/1953 | Slaybaugh | 424/4 |
| 2,940,996 | 6/1960 | Papa | 424/5 X |
| 2,996,433 | 8/1961 | Hoppe et al. | 424/4 X |
| 3,359,278 | 12/1967 | Wallingford | 424/5 X |
| 3,553,260 | 1/1971 | Felder et al. | 424/5 X |
| 3,666,803 | 5/1972 | Haltermann | 424/5 X |

FOREIGN PATENT DOCUMENTS

1,437,666   3/1966   France ..................... 424/5

OTHER PUBLICATIONS

Hackh's Chemical Dictionary, 3rd Ed., The Blakiston Co., Philadelphia, (1944), p. 779.

*Primary Examiner*—Albert T. Meyers
*Assistant Examiner*—Vera C. Clarke
*Attorney, Agent, or Firm*—Millen & White

[57] ABSTRACT

An oral dosage form of X-ray contrast medium for cholecystocolangiography comprises a constrast agent and an amount of a pharmaceutically acceptable base, sufficient to neutralize the stomach acid of the person ingesting it.

17 Claims, No Drawings

ORAL DOSAGE FORM FOR X-RAY CONTRAST MEDIA CONTAINING A PHARMACEUTICALLY ACCEPTABLE BASE AND METHOD OF USE THEREOF

BACKGROUND OF THE INVENTION

X-ray contrast media heretofore usable orally for cholecystocholangiography do not have the diagnostic value of intraveneously administered X-ray contrast media, although the former are more readily administered and better tolerated. X-ray examination can generally be conducted only 12–14 hours after ingestion of the contrast medium, due to slow absorption. Roentgenological visualization of the gall bladder provides less contrast than with intravenously administered X-ray contrast media. Extrahepatic bile ducts are normally detected only when a so-called double dose is used, in a low percentage of cases.

Therefore, there is a continuing need for an orally administered dosage form of X-ray contrast media having a very high contrast effect, so that the bile ducts and gall bladder are visualized simultaneously and maximum accumulation of contrast agent in the receptor organ takes place more rapidly than heretofore and is also more accurately predictable in time.

An attempt was made to introduce the contrast medium into the intestine with a large liquid volume administered simultaneously and to improve the resorption rate by administration of metoclopramide i.v. The control group received contrast media without additives. This experiment was unsuccessful in overcoming the known disadvantages of conventional X-ray contrast media.

SUMMARY OF THE INVENTION

In a compositional aspect, this invention relates, in an X-ray contrast medium adapted for oral administration comprising an X-ray contrast agent for cholecystocholangiography, in admixture with a pharmaceutically acceptable carrier, to the improvement wherein the contrast medium comprises an amount of a pharmaceutically acceptable base sufficient to neutralize the stomach acid content of a human.

In a method-of-use aspect, this invention relates to a method for orally administering an X-ray contrast medium for cholecystocholangiography comprising administering orally to the patient concurrently with the contrast medium an amount of a physiologically acceptable base sufficient to neutralize the stomach acid.

DETAILED DESCRIPTION

Simultaneous oral administration of sodium bicarbonate as a physiologically compatible base with a contrast agent accelerates resorption of the contrast agent in a statistically significant manner, as illustrated by the experimental protocol of Table I, using as an exemplary contrast medium succinic acid mono-2,4,6-triiodo-3-methylamino-N-ethylanilide.

TABLE I

Comparison of the Blood Levels of Contrast Medium of Four Patient Groups after Oral Administration of 3 g. of Succinic Acid Mono-2,4,6-triiodo-3-methylamino-N-ethylanilide as a Microcrystal Suspension with Various Additional Treatments (I = No Treatment; II = 350 ml. of Tea, III = 10 mg. of Metoclopramide i.v.; and IV = g. of Sodium Bicarbonate)

| Group | Additional Treatment | Blood Level $t_{max}$ (Min. per appl.) | $C_{max}$ (mg/100 ml) | (% of Dose in Bl. Vol.) |
|---|---|---|---|---|
| I | None | 132 ± 24 | 11.4 ± 4.5 | 23 ± 8 |
| II | 350 ml. Tea | 120 ± 24 | 10.4 ± 4.2 | 23 ± 11 |
| III | 10 mg. Metoclopramide | 96 ± 12 | 9.7 ± 2.9 | 30 ± 10 |
| IV | 3 g. Na Bicarb. | 54 ± 12 | 9.8 ± 2.6 | 33 ± 3 |

$t_{max}$ = Time of maximum blood level
$C_{max}$ = Maximum concentration in mg/100 ml and % of dose in the total blood volume, respectively
Average values ± standard deviation From Table I, it is seen that administration of metoclopramide (4-amino-5-chloro-N-(2-diethylaminoethyl)-2-methoxy-benzamide) produces no detectable improvement over the control. However, after administration of 3 g. of sodium bicarbonate, the maximum blood level is attained within 54 ± 12 minutes after administration. Within 30 minutes after ingestion, the blood level has risen, on the average, to 80% of the maximum value.

The difference compared to the groups which received no base/buffer, 350 ml. of tea or 10 mg. of metoclopramide, respectively, is significant. The early attainment of maximum blood level permits calculation of elimination half life of contrast medium from the blood, which varies according to the idiosyncrasies of the patients to an average of 138 ± 84 minutes. From the elimination half life and the time of the maximum blood level, the resorption half life is calculated as 18 ± 6 minutes.

The invention relates to novel oral X-ray contrast media, which contain at least one contrast agent in combination with a physiologically compatible base. The term "combination" is understood to mean the contrast agent and the base represent a dosage unit which can be administered together or separately.

Using the X-ray contrast media of this invention, a high-contrast reproduction of the gall bladder and the bile ducts is made possible simultaneously and at an exactly predictable time. Moreover, visualization of the bile ducts is attained with 2 single dose (~3 g. of contrast medium).

Suitable contrast media include all orally administrable X-ray contrast media for cholecystocholangiography. The contrast agents for such contrast media preferably are polyiodoaromatic compounds.

Examples of suitable polyiodoaromatic compounds are N-methyl-N-(3-amino-2,4,6-triiodophenyl)-glutaric acid monoamide, N-(3-amino-2,4,6-triiodophenyl)-3-acetamido-2-methyl-propionic acid.

Most preferably, polyiodoaromatic acids on their salts are used as orally-administered X-ray contrast agents in the practice of this invention.

Salts are preferably alkali metal salts. Examples of preferred contrast agents are: succinic acid mono-2,4,6-triiodo-3-methylamino-N-ethylanilide; 2-(3-amino-2,4,6-triiodobenzyl)-butyric acid (iopanoic acid); the sodium salt of 2-(3-butyramido-2,4,6-triiodobenzyl)- butyric acid (Na tyropanoate); the sodium salt of β-[3-(dimethylaminomethyleneamino)-2,4,6-triiodophenyl]-propionic acid (Na iopodate); N-(3-amino-2,4,6-triiodobenzoyl)-N-phenyl-β-aminopropionic acid (iobenzamic acid); and the sodium salt of α-ethyl-β2-(3-acetamido-2,4,6-triiodophenoxy)-ethoxy]-propionic acid (sodium iopronate).

Suitable physiologically compatible bases/buffers are the salts of weak acids and strong bases, e.g., combinations of the following ions: $Li^+$, $Na^+$, $K^+$, $Mg^{2+}$, $Ca^{2+}$ and $CO_3^{2-}$, $HCO_3^-$, $CH_3COO^-$, $PO_4^{3-}$, $HPO_4^{2-}$, $H_2PO_4^-$, tris-ethanolamine, methylglucamine, and others. Carbonates and bicarbonates, for example, $NaHCO_3$, $MgCO_3$, $Na_2CO_3$, are preferred, individually or in the form of mixtures.

The pharmacologically acceptable base is used in quantities sufficient to completely neutralize the content of stomach acid of the patient and optionally to provide the cation for the contrast medium acid. For a contrast medium dose of about 3–10 g., approximately 0.5–10 g., preferably 3–6 g., of buffer is utilized. For example, very good results are achieved with 3–4 g. of $NaHCO_3$ and a simultaneous dose of 3 g. of contrast medium acid.

The novel oral X-ray contrast media are prepared in accordance with methods generally known to those skilled in the art. For example, contrast agents are mixed with a physiologically compatible base/buffer or buffer mixture with the customary galenic auxiliary agents or the contrast medium and the physiologically compatible base/buffer or buffer mixture are compounded separately with conventional galenic adjuvants and converted to the ultimately desired dosage form.

Examples of auxiliary agents are: sucrose, highly disperse silicon dioxide, polyoxyethylene-polyoxypropylene polymers, amylose, magnesium stearate, sodium lauryl sulfate, talc, sugar, silicates, cellulose, methyl cellulose, polyvinylpyrrolidone, etc.

The forms customary in galenic pharmacy for enteral administration include suspensions, dragees, tablets, capsules, and powders.

By administering the compositions of the present invention, results are attained which have heretofore been impossible to obtain by an orally administered X-ray contrast medium.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(Composition as a Powder)

| | | |
|---|---|---|
| (a) | Succinic acid mono-2,4,6-triiodo-3-methylamino-N-ethylanilide, micronized | 3.000 g. |
| | Sucrose | 4.895 g. |
| | Polyoxyethylene-polyoxypropylene polymer | 0.100 g. |
| | Aromatic substances | 0.005 g. |
| | | 8.000 g. |
| (b) | $NaHCO_3$ as a powder or tablet | 3.000 g. |

EXAMPLE 2

(Composition as a Powder)

| | | |
|---|---|---|
| (a) | Succinic acid mono-2,4,6-triiodo-3-methylamino-N-ethylanilide / tris | 3.580 g. |
| | Sucrose | 4.895 g. |
| | Polyoxyethylene-polyoxypropylene polymer | 0.100 g. |
| | Aromatic substances | 0.005 g. |
| | | 8.580 g. |
| (b) | ($NaHCO_3$ as a powder or tablet | 2.500 g. |

EXAMPLE 3

(Composition as a Powder)

| | |
|---|---|
| Succinic acid mono-2,4,6-triiodo-3-methylamino-N-ethylanilide, micronized | 3.000 g. |
| $NaHCO_3$  < 0.3 mm. | 3.000 g. |
| Sucrose | 4.895 g. |
| Polyoxyethylene-polyoxypropylene polymer | 0.100 g. |
| Aromatic substances | 0.005 g. |
| | 11.000 g |

EXAMPLE 4

(Composition as a Powder)

| | |
|---|---|
| Succinic acid mono-2,4,6-triiodo-3-methylamino-N-ethylanilide / tris | 3.580 g. |
| $NaHCO_3$  < 0.3 mm. | 2.500 g. |
| Sucrose | 4.895 g. |
| Polyoxyethylene-polyoxypropylene polymer | 0.100 g. |
| Aromatic substances | 0.005 g. |
| | 11.080 g. |

EXAMPLE 5

(Composition as a Tablet)

| | | |
|---|---|---|
| (a) | Succinic acid mono-2,4,6-triiodo-3-methylamino-N-ethylanilide | 500.0 mg. |
| | Magnesium stearate | 3.0 mg. |
| | Highly disperse $SiO_2$ | 3.0 mg. |
| | Cellulose | 100.0 mg. |
| | Lactose | 94.0 mg. |
| | | 700.0 mg. |
| (b) | $NaHCO_3$ as a tablet | 500.0 mg. |

Six tablets per dose.

EXAMPLE 6

(Composition as a Tablet)

| | |
|---|---|
| Succinic acid mono-2,4,6-triiodo-3-methylamino-N-ethylanilide | 500.0 mg. |
| $NaHCO_3$ | 290.0 mg. |
| Cellulose | 95.0 mg. |
| Talc | 10.0 mg. |
| Magnesium stearate | 5.0 mg. |
| | 900.0 mg. |

Six tablets per dose.

In each of Examples 1–6, a chemical equivalent of $KHCO_3$, $Na_2CO_3$ or $K_2CO_3$ can be substituted for the $NaHCO_3$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a pharmaceutical composition adapted for oral administration, comprising in unit dosage form, an X-ray contrast agent for cholecystocholangiography in admixture with a pharmaceutically-acceptable carrier, the improvement wherein the composition comprises an amount per unit dosage of a pharmaceutically-acceptable base effective to neutralize the stomach acid content of a human when the composition is ingested.

2. The composition of claim 1, wherein the contrast agent is a polyiodoaromatic acid or salt thereof.

3. The composition of claim 1, wherein the amount of base is 0.5–10 g.

4. The composition of claim 1, in tablet or powder form.

5. The composition of claim 1, which contains, per dosage unit, 3–10 g. of the contrast agent and 0.5–10 g. of the base.

6. The composition of claim 1, wherein the contrast agent is succinic acid mono-2,4,6-triiodo-3-methylamino-N-ethylanilide.

7. The composition of claim 1, wherein the base is $NaHCO_3$.

8. The composition of claim 6, wherein the base is $NaHCO_3$.

9. A method for orally administering an X-ray contrast medium for cholecystocholangiography comprising administering orally to the patient concurrently with the contrast agent an amount of a physiologically-acceptable base sufficient to neutralize the stomach acid content of said patient.

10. The method of claim 9, wherein the contrast agent is a polyiodoaromatic acid or salt thereof.

11. The method of claim 9, wherein the contrast agent and the base are administered in one unitary dosage.

12. The method of claim 9, wherein the contrast agent and the base are administered in separate unitary dosages.

13. The method of claim 9, wherein the contrast agent is succinic acid mono-2,4,6-triiodo-3-methylamino-N-ethylanilide.

14. The method of claim 9, wherein the base is $NaHCO_3$.

15. The method of claim 13, wherein the base is $NaHCO_3$.

16. The method of claim 9, wherein the dosage of the base is 0.5–10 g.

17. The method of claim 11, wherein the unitary dosage contains 3–10 g. of the contrast agent and 0.5–10 g. of the base.

* * * * *